United States Patent [19]
Lupi-Chen et al.

[11] Patent Number: 5,910,575
[45] Date of Patent: *Jun. 8, 1999

[54] IMMUNOASSAY AND MONOCLONAL ANTIBODIES FOR URINARY CORTISOL

[75] Inventors: Nina Lupi-Chen, Marseilles; Elisabeth Mappus, Ste Foy les Lyon; Catherine Fournier, Villeurbanne; Christophe Barrande; Sandrine Portuesi, both of Marseilles; Yves-Claude Cuilleron, Ste Foy les Lyon, all of France

[73] Assignees: Immunotech, Marseille, France; Inserm, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/620,337

[22] Filed: Mar. 22, 1996

[30] Foreign Application Priority Data

Mar. 24, 1995 [FR] France .................................. 95.03749

[51] Int. Cl.$^6$ .................................................. C07K 16/00
[52] U.S. Cl. ................................ 530/388.24; 530/388.1; 530/389.1; 530/389.8; 530/389.9; 435/7.1; 435/975; 436/547; 436/548
[58] Field of Search ........................... 530/388.24, 388.1, 530/389.1, 389.8, 388.9; 435/7.1, 975; 436/547, 548

[56] References Cited

U.S. PATENT DOCUMENTS 4,339,390  7/1982  Ali et al. .
4,366,143  12/1982  Midgley et al. ........................ 436/501

FOREIGN PATENT DOCUMENTS 2 537 586 A1  12/1982  France .
27 20 809 A1  5/1977  Germany .

OTHER PUBLICATIONS

Philomin et al., "New Applications of Carbonylmetalloimmunoassay (CMIA): A Non–Radioisotopic Approach to Cortisol Assay," Journal of Immunological Methods, 171:201–210, 1994.
Norbert W. Tietz (ed), Textbook of Clinical Chemistry (WB Saunders Company—Philadelphia), p. 1073, 1986.
Hampl et al, Recent Advances in Immunoassay of Steroid Hormones, TRAC vol. 8, No. 2, pp. 72–75, Feb. 1989.

*Primary Examiner*—James C. Housel
*Assistant Examiner*—Bao-Thuy L. Nguyen
*Attorney, Agent, or Firm*—Browdy and Neimark

[57] ABSTRACT

A polyclonal or monoclonal antibody recognizing specifically cortisol in a urine medium produced by immunization of animals against an immunogen compound composed of the hapten cortisol-3-carboxymethyloxime (syn isomer), coupled by its carboxyl function to a macromolecule, an immunoasay process for cortisol, particularly urinary cortisol, an assay kit and novel derivatives of coritsol.

8 Claims, 2 Drawing Sheets

IMMUNOASSAY AND MONOCLONAL ANTIBODIES FOR URINARY CORTISOL

BACKGROUND OF THE INVENTION

1. Field of the Invention

The present invention relates to a new immunoassay process for cortisol involving neither extraction nor chromatography, based on the surprising properties of certain antibodies directed against cortisol.

The invention provides in particular the antibodies themselves, a process for obtaining them, assay processes for cortisol based on these antibodies, and kits of reagents allowing the use of said processes.

2. Description of the Background Art

Cortisol, the principal glucocorticoid hormone, is synthesized in the fascicular and reticular zones of the adrenal cortex. It is derived from cholesterol under the influence of several enzymes. Its rate of secretion is under hypothalamic-pituitary control. CRF (Corticotropin Releasing Factor) activates the anterior pituitary which produces ACTH, which in turn stimulates the adrenal cortex which synthesizes corticoids, of which 90% is cortisol. In the plasma, the majority of the cortisol circulates in the form bound to plasma proteins: mainly to corticosteroid binding globulin, to albumin and to testosterone estradiol binding globulin; a very small proportion exists in the free form.

A functional exploration of the hypothalamus-pituitary-adrenal cortex axis is largely based on the determination of cortisol. The measurement of cortisol in serum is used essentially during dynamic tests. Free urinary cortisol exhibits a good correlation with the rate of production of the hormone and remains the best hormonal index in cases of hyperadrenocorticism.

The direct determination of cortisol in serum is facilitated by its generally high level in comparison with all the other steroids, with the exception of dehydro-epiandrosterone (DHEA) sulphate which belongs to the family of androgens with a very different structure and is hardly recognized at all by anti-cortisol antibodies. All the radioimmunoassay or enzyme-immunoassay kits on the market propose techniques for the direct measurement of cortisol in sera. They are often of the desired quality (see Table 1 below).

On the other hand, the direct determination of urinary cortisol is a more difficult operation due essentially to the accumulation of metabolites, of which little is often known about their structure and concentration. Until now, the most reliable assay processes for cortisol in this biological medium include an extraction stage with dichloromethane followed by chromatography which ensures specificity. These operations are delicate, long and expensive.

Numerous attempts have been made to produce monoclonal and polyclonal anti-cortisol antibodies, particularly from a cortisol-21-hemisuccinate derivative and above all from a cortisol-3-CMO derivative, without any description in this latter case of specific properties associated with the syn/anti geometrical isomerism of the CMO group. Such antibodies do not permit a correct determination of urinary cortisol: they overestimate the concentrations of cortisol in the urine compared with the results obtained by determination after chromatography.

Three manufacturers: Kodak, Orion and DSL propose the direct determination of urinary cortisol. However, as Table 2 below shows, these processes give very different results from those obtained by determination after extraction and chromatography of the sample.

It would be desirable, therefore, to have a rapid method for the direct measurement of urinary cortisol which gives a result similar to the one obtained by chromatography, a method which is too cumbersome for routine use.

SUMMARY OF THE INVENTION

The applicant prepared certain antibodies and discovered that these, antibodies whether polyclonal or monoclonal, present a particular specificity which permits a direct determination not only of cortisol in serum and other biological fluids (saliva, cerebrospinal fluid, culture supernatants) but also of cortisol in the urine.

Said antibodies according to the invention may be obtained in particular from animals immunized with a new immunogen composed of the hapten cortisol-3-carboxymethyloxime (syn isomer), coupled to a macromolecule.

For this reason, the object of the present invention is a novel polyclonal or monoclonal antibody that specifically recognizes cortisol in a urine medium, produced by immunization of animals against an immunogen compound composed of the hapten cortisol-3-carboxymethyloxime (a substantially pure syn isomer), coupled by its carboxyl function to a macromolecule. Cortisol-3-carboxymethyloxime will sometimes be referred to hereinafter as cortisol-3-CMO.

DESCRIPTION OF THE INVENTION

Figure 1:
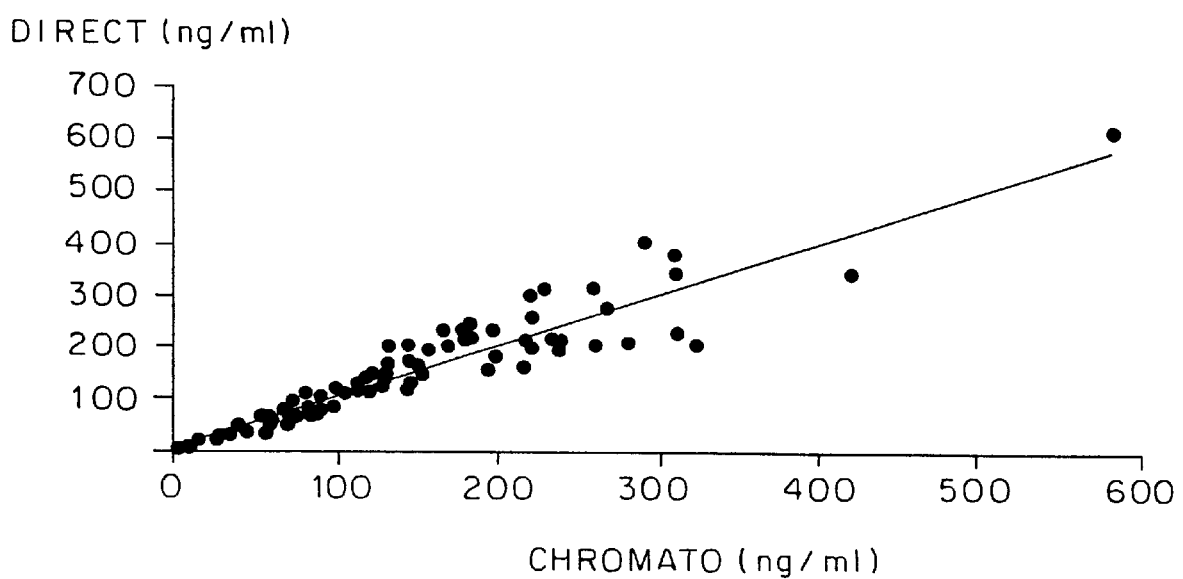
FIG. 1 shows the correlation between the method of direct determination of cortisol according to the present invention and a method of determination of cortisol after chromatography.

The term "macromolecule" means in particular a protein or a polysaccharide with a sufficient molecular weight to induce the production of antibodies in animals, and preferably bovine serum albumin (BSA). According to most authors, a molecular weight of 5000 is considered to be sufficient.

The term "coupled" means that cortisol-3-CMO (syn) is coupled to the macromolecule in particular by a covalent bond, for example ester or amide, and preferably an amide bond to the lysines of a protein.

Another way of defining such antibodies with a view to an application to the determination in urine is to characterize them by affinity for the cortisol-3-carboxymethyloxime (syn) derivative coupled to histamine, which is equal to or greater than their affinity for the cortisol-3-carboxymethyloxime (anti) derivative coupled to histamine, the ratio of affinities being preferably greater then 1.5.

A particular embodiment of the invention consists in coupling cortisol-3-carboxymethyloxime (syn) to bovine serum albumin (BSA) with a coupling molar ratio greater than or equal to 1 and preferably between 15 and 31. In this way, polyclonal antibodies are produced in mice with a great affinity and remarkable specificity, permitting the direct determination of cortisol in the urine of patients, involving neither extraction nor chromatography, within a period of one hour.

Myeloma cells of mice have also been fused with lymphocytes of mice that have been immunized with the immunogen cortisol-3-carboxymethyloxime (syn)-BSA to produce monoclonal antibodies, the specificity of which is virtually identical to that of the corresponding polyclonal antibodies.

The present invention therefore provides in particular such monoclonal antibodies, particularly a monoclonal antibody secreted by the hybridoma IMMU-473, filed and deposited on Feb. 9, 1995 under no. I 1532 with the Collection Nationale des Cultures de Microorganismes in Paris.

The antibodies described above and used in the processes and kits below are preferably monoclonal.

The process for obtaining antibodies according to the invention described above is not limiting. In particular, it is possible to obtain antibodies according to the invention with mixed immunogens, with carriers that are not macromolecules, by immunization in vitro, or even without immunization (Griffiths A. D. et al.; EMBO Journal, 13, 3245–3260, 1994).

The invention also provides assay processes for cortisol based on the polyclonal or monoclonal antibodies described above in various assay techniques using radioactive labels (tritium or radioactive iodine, for example), enzyme, luminescent or fluorescent labels, in the solid or the liquid phase. Such labels may be attached either to a derivative of cortisol or to a monoclonal or polyclonal antibody according to the invention, in order to produce the corresponding tracer. Tritiated cortisol or a derivative of tritiated cortisol may also constitute a suitable tracer.

For this reason, the present invention also provides an immunoassay process for cortisol characterized in that an antibody as defined above is used, the assay is a competitive assay using a tracer and in that the tracer is composed of the hapten cortisol-3-carboxymethyloxime (syn) or cortisol-3-carboxymethyloxime (anti) coupled by its carboxyl function to a label which is a molecule capable of being iodinated.

Coupling may be direct or achieved by way of an arm well known in the state of the art.

The term "molecule capable of being iodinated" means a molecule capable of being iodinated that is well known to the man skilled in the art, for example, histamine, histidine, tyramine, tyrosine or a peptide containing a residue capable of being iodinated, such as a phenol or imidazole nucleus.

A particular embodiment of the invention consists in using an antibody described above fixed to a solid phase which is incubated in the presence of the cortisol to be determined and a radioactive iodinated tracer produced by labelling with iodine-125 a precursor obtained by grafting cortisol-3-carboxymethyloxime (syn) or cortisol-3-carboxymethyloxime (anti) to an above-mentioned molecule capable of being iodinated.

Under other preferential conditions of using the invention, the above process is characterized in that, by way of a tracer, cortisol-3-carboxymethyloxime (syn) or cortisol-3-carboxymethyloxime (anti) is coupled to radioactive iodinated histamine.

Under preferential conditions of use, the process described above is characterized in that the radioactive tracer is iodinated with iodine-125.

According to other immunoassay techniques, the cortisol to be determined competes with a tracer which is a conjugate composed of cortisol-3-carboxymethyloxime (syn) or cortisol-3-carboxymethyloxime (anti) coupled to an enzyme or to a luminescent or fluorescent molecule.

The polyclonal or monoclonal antibodies according to the invention are preferably fixed to a solid phase, tubes, titration plates or beads.

The invention also provides an immunoassay process for cortisol in which a cortisol derivative is used, in particular cortisol-3-carboxymethyloxime (syn or anti) fixed to a solid phase and an anti-cortisol antibody as defined above, labelled by a radioactive, enzyme, luminescent or fluorescent molecule.

In this latter process, the cortisol to be determined is incubated in the presence of an immobilized cortisol derivative mentioned above and an antibody according to the invention which has been labelled.

The present invention also provides assay kits for cortisol in biological fluids using an antibody as defined above.

A first type of kit for the direct determination of cortisol comprises a solid phase coated with antibodies directed against cortisol-3-carboxymethyloxime (syn)-BSA according to the invention.

A kit of this kind also includes preferably a "cortisol-3-carboxymethyloxime (anti)" or "cortisol-3-carboxymethyloxime (syn)" tracer coupled by its carboxyl function either to an enzyme or to a fluorescent or luminescent molecule or to a histamine or to a peptide or to an amino acid derivative comprising a phenol nucleus or an imidazole nucleus, iodinated by a radioactive iodine atom. An even more complete kit also comprises advantageously one or preferably two standard ranges of cortisol, one for the determination of cortisol in urine, the other for the determination of cortisol in sera.

A second type of kit for the direct determination of cortisol contains an "anti-cortisol antibody" tracer according to the invention, labelled either with radioactive iodine or by a luminescent or fluorescent molecule or by an enzyme. A kit of this kind also preferably includes a solid phase coated with cortisol antigen and also, advantageously, one or preferably two standard ranges of cortisol, one for the determination of cortisol in urine, the other for the determination of cortisol in sera.

The invention also provides cortisol-3-carboxymethyloxime (syn)-histamine and cortisol-3-carboxymethyloxime (anti)-histamine, in the substantially pure form, which may be used for the characterization of the antibodies and as precursors of radioactive iodinated derivatives.

The invention also provides cortisol-3-carboxymethyloxime (syn), in the substantially pure form, cortisol-3-carboxymethyloxime (anti), in the substantially pure form, and in particular cortisol-3-carboxymethyloxime (syn), in the substantially pure form, which may be enriched with majority isomer in a quantity of at least 96%, particularly substantially free from cortisol-3,20-dicarboxymethyloxime, that is, containing less than 1%, and containing preferably less than 1% of transformation products of the functions in the 11 position and on the dihydroxyketone side chain in the 17 position (percentages estimated by high performance liquid chromatography) and more particularly cortisol-3-carboxymethyloxime (anti) enriched with majority isomer in a quantity of at least 99%, particularly substantially free from cortisol-3,20-dicarboxymethyloxime, that is, containing less than 1%, and containing less than 1% of transformation products of the functions in the 11 position and on the dihydroxyketone side chain in the 17 position (percentages estimated by high performance liquid chromatography).

Finally, the invention provides cortisol-3-carboxymethyloxime (syn) coupled to a macromolecule, particularly to a protein, particularly to bovine serum albumin.

Conditions under which the hybridomas that secrete monoclonal antibodies according to the invention have been isolated will be described below.

Also to be found below are examples illustrating the direct determinations of cortisol in sera and urine, of the competitive radioimmunoassay type, with the aid of these monoclonal antibodies. These examples relate to:

1. The synthesis of the hapten cortisol-3-CMO and separation of the syn and anti isomers.
2. The preparation of the immunogen cortisol-3-CMO (syn)-bovine serum albumin.
3. The preparation of the immunogen cortisol-3-CMO (anti)-bovine serum albumin.
4. The preparation of the labelling precursor: cortisol-3-CMO (syn)-histamine and the corresponding radioactive iodinated tracer.
5. The preparation of the labelling precursor: cortisol-3-CMO (anti)-histamine and the corresponding radioactive iodinated tracer.
6. Antibodies directed against cortisol-3-CMO (syn)-BSA.
7. A kit for the direct determination of cortisol in sera or plasma.
8. A kit for the direct determination of cortisol in urine.

EXAMPLE 1

Synthesis of Cortisol-3-CMO and Separation of the Two Syn and Anti Isomers

Stage A: 21-acetoxycortisol

Cortisol (10.0 g; 27.6 mmol) is dissolved in 300 ml of a 5:1 mixture of pyridine-acetic anhydride. The reaction mixture is kept at 70° C. for 75 minutes then evaporated under reduced pressure. The final traces of acetic anhydride are removed by the addition of ethanol and by azeotropic distillation of toluene under reduced pressure. The acetate is obtained in the form of a white solid (11.1 g; 27.4 nummol).

$R_f$=0.35 (chloroform-ethyl acetate 1:1)

m.p.=220–224° C. (after recrystallization in a mixture of chloroform and methanol).

$^1$H-NMR ($C_5D_5N$) $\delta$1.41 (3H, s, 18-$CH_3$); 1.62 (3H, s, 19-$CH_3$); 2.12 (3H, s, 21-$COCH_3$); 4.7 (1H, m, 11α-H); 5.3–5.6 (4H, q: J=17.5 Hz, 21-$CH_2O$); 5.8 (1H, s, 4-H).

Stage B: 21-acetoxycortisol-3-CMO (Syn+Anti Mixture)

The 21-acetoxycortisol (4.0 g; 9.9 mmol) obtained in stage A is dissolved in 150 ml of anhydrous pyridine. A solution of O-carboxymethylhydroxylamine hemihydrochloride (1.3 g; 5.9 mmol) in 150 ml of pyridine is added dropwise to this solution. The reaction medium is agitated under a nitrogen atmosphere for 16 hours at ambient temperature. The end of the reaction is verified by thin layer chromatography, then the pyridine is removed by evaporation under reduced pressure. The residue is absorbed with a saturated aqueous solution of sodium hydrogen carbonate which is then extracted with chloroform to remove the non-acid contaminants. The aqueous phase is acidified to pH 4 by the addition of hydrochloric acid and extracted with ethyl acetate. The organic phase containing the steroid is evaporated then dried by azeotropic distillation of toluene, under reduced pressure.

The product obtained is 21-acetoxycortisol-3-CMO (4.3 g; 9.0 mmol) containing a mixture of syn and anti isomers (40% and 60% respectively, percentages estimated by NMR).

$R_f$=0.40 (syn) and 0.50 (anti) (chloroform-acetone-acetic acid 7:2:1)

$^1$H-NMR ($C_5D_5N$) $\delta$1.38 (3H, s, 18-$CH_3$); 1.53 (3H, s, 19-$CH_3$); 2.11 (3H, s, 21-$COCH_3$); 4.6 (1H, m, 11α-H); 5.1 (2H, s, $NOCH_2CO$); 5.3–5.6 (4H, q: J=17.5 Hz, 21-$CH_2O$); 6.0–6.7 (1H, s, 4-H anti and syn).

Stage C: Cortisol-3-CMO (Syn+Anti Mixture)

The mixture of syn and anti isomers of 21-acetoxycortisol-3-CMO (2.0 g; 4.2 mmol) obtained in stage B is dissolved in 320 ml of methanol, then 20 ml of a 10% aqueous solution of potassium hydrogen carbonate is added. The reaction mixture is agitated for 16 hours under a nitrogen atmosphere at ambient temperature, then evaporated under reduced pressure. The residue is absorbed with 100 ml of water and the solution is acidified to pH 4 by the addition of hydrochloric acid, then extracted with ethyl acetate. The organic phase containing the steroid is evaporated then dried by azeotropic distillation of toluene, under reduced pressure.

The product obtained is cortisol-3-CMO (1.6 g; 3.7 mmol) containing a mixture of syn and anti isomers (40% and 60% respectively, percentages estimated by NMR).

$R_f$=0.19 (syn) and 0.27 (anti) (chloroform-acetone-acetic acid 7:2:1).

Stage D: Syn Isomer and Anti Isomer of Cortisol-3-CMO

The two syn and anti isomers of the cortisol-3-CMO derivative (0.48 g; 1.1 mmol) obtained in stage C are separated by chromatography on silica plates developed by a mixture of chloroform-acetone-acetic acid 7:2:1. 0.17 g (0.39 mmol) of syn isomer and 0.21 g (0.48 mmol) of anti isomer are obtained, each containing between 5 and 10% of the other isomer. Each isomer is then obtained in the pure state by high performance liquid chromatography (HPLC) using a Waters C18 column; eluant: methanol-water-acetic acid 600:400:1; flow rate 8 ml/minute; $t_r$ (anti)=23 minutes, $t_r$ (syn)=26 minutes. The solvent is then evaporated under reduced pressure.

Isomer (Syn) of Cortisol-3-CMO $R_f$=0.19 (chloroform-acetone-acetic acid 7:2:1)
m.p.=133 –136° C. (crude product separated by HPLC)
UV: $\lambda_{max}$=256 nm; $\epsilon$=15000 $M^{-1}cm^{-1}$
$^1$H-NMR ($CD_3OD$) $\delta$0.86 (3H, s, 18-$CH_3$); 1.37 (3H, s, 19-$CH_3$); 4.2–4.7 (4H, q: J=19 Hz, 21-$CH_2O$); 4.4 (1H, m, 11α-H); 4.5 (2H, s, $NOCH_2CO$); 6.4 (1H, s, 4-H).

Isomer (Anti) of Cortisol-3-CMO $R_f$=0.27 (chloroform-acetone-acetic acid 7:2:1)
m.p.=223 –227° C. (crude product separated by HPLC)
UV: $\lambda_{max}$ 250 nm; $\epsilon$=23000 $M^{-1}cm^{-1}$
$^1$H-NMR ($CD_3OD$) $\delta$0.86 (3H, s, 18-$CH_3$); 1.34 (3H, s, 19-$CH_3$);4.2–4.7 (4H, q: J=19 Hz, 21-$CH_2O$); 4.4 (1H, m, 11α-H); 4.5 (2H, s, $NOCH_2CO$); 5.6 (1H, s, 4-H).

EXAMPLE 2

Immunogen: Isomer (Syn) of Cortisol-3-CMO Coupled to Bovine Serum Albumin

Stage A: Isomer (Syn) of Cortisol-3-CMO Activated in the Form of N-hydroxysuccinimide Ester The isomer (syn) of cortisol-3-CMO (0.1 g; 0.23 mmol) obtained in stage D of example 1 is dissolved in 20 ml of anhydrous THF in the presence of N-hydroxysuccinimide (0.11 g; 0.95 mmol) and dicyclohexylcarbodiimide (0.21 g; 1.02 mmol). The reaction mixture is agitated for 4 hours at ambient temperature under a nitrogen atmosphere and in darkness, then filtered. The filtrate is evaporated to dryness under a stream of nitrogen without heating to give the crude activated ester which may generally be used in that form for the rest of the process.

$R_f$=0.54 (ethyl acetate)

Stage B: Immunogen: Isomer (Syn) of Cortisol-3-CMO Coupled to Bovine Serum Albumin The bovine serum albumin (200 mg; approx. 3 $\mu$mol) is dissolved in 8 ml of a 10 mM aqueous solution of sodium hydrogen carbonate to which 3 ml of THF are added dropwise. The isomer (syn) of cortisol-3-CMO activated in the form of N-hydroxysuccinimide ester (0.06 g; 113 $\mu$mol) obtained in stage A is dissolved in 3 ml of THF. This solution is then added dropwise to the solution of bovine serum albumin. The reaction mixture is agitated at ambient temperature for 16 hours, then dialysed at +4° C. against a 10 mM aqueous solution of sodium hydrogen carbonate. The dialysate is separated by chromatography using a SEPHAROSE CL 4B column (Pharmacia), a cross-linked agarose matrix with an agarose content of 4% equilibrated with a 10 mM aqueous solution of sodium hydrogen carbonate (detection by absorbance of UV at 280 nm). The fractions containing the immunogen are pooled, dialysed against deionised water adjusted to pH 7 by the addition of ammonium hydrogen carbonate, and freeze-dried.

Approximately 250 mg of the immunogen isomer (syn) of cortisol-3-CMO coupled to bovine serum albumin are obtained, the coupling ratio being between 27 and 31. The name of the compound is abbreviated to cortisol-3-CMO (syn)-BSA.

EXAMPLE 3

Immunogen: Isomer (Anti) of Cortisol-3-CMO Coupled to Bovine Serum Albumin

Stage A: Isomer (Anti) of Cortisol-3-CMO Activated in the Form of N-hydroxy-succinimide Ester The anti isomer of cortisol-3-CMO obtained in stage D of example 1 is treated as indicated in stage A of example 2 to obtain the crude activated ester.

$R_f$=0.61 (ethyl acetate)

Stage B: Immunogen: Isomer (Anti) of Cortisol-3-CMO Coupled to Bovine serum Albumin The isomer (anti) of cortisol-3-CMO activated in the form of N-hydroxysuccinimide ester obtained in stage A is treated in the same way as indicated in stage B of example 2 to obtain the expected immunogen: cortisol-3-CMO (anti)-BSA, the coupling ratio of which is between 27 and 31.

EXAMPLE 4

Labelling Precursor: Isomer (Syn) of Cortisol-3-CMO Coupled to Histamine and the Corresponding Radioactive Iodinated Tracer

Stage A: Isomer (Syn) of Cortisol-3-CMO Attached to Histamine

The basic histamine (0.05 g; 0.45 mmol) is dissolved in 1 ml of a 10 mM aqueous solution of sodium hydrogen carbonate, then 1 ml of THF is added. The isomer (syn) of cortisol-3-CMO activated in the form of N-hydroxysuccinimide ester (0.03 g; 0.056 mmol) obtained in stage A of example 2 is dissolved in 1.5 ml of THF. This solution is added dropwise to the histamine solution. The reaction mixture is agitated at ambient temperature under a nitrogen atmosphere for 1 hour. The solution is adjusted to pH 7 by the addition of hydrochloric acid then evaporated to dryness under reduced pressure. The residue is then purified by chromatography over silica plates developed in a 60:10:2 mixture of chloroform-methanol-ammonia then by HPLC (Shandon Ultrabase 5$\mu$ column, $\mu$Bondapak C18; eluant: methanol-water-ammonia 500:500:1; flow rate 1 ml/minute); $t_r$ (syn)-25.3 minutes.

0.02 g (0.038 mmol) of product coupled to histamine is obtained. The name of this product is abbreviated to cortisol-3-CMO (syn)-histamine.

$R_f$=0.25 (chloroform-methanol-ammonia 60:10:2)

m.p.=126 –131° C. (crude product separated by HPLC)

UV: $\lambda_{max}$=253 nm; $\epsilon$=15000 $M^{-1}cm^{-1}$ $^1$H-NMR (CD$_3$OD) $\delta$0.87 (3H, s, 18-CH$_3$); 1.38 (3H, s, 19-CH$_3$); 2.8, 3.5 (2H each, t: J=7 Hz each, CH$_2$–CH$_2$-histamine); 4.2–4.7 (4H, q: J=19 Hz, 21-CH$_2$O); 4.4 (1H, m, 11$\alpha$-H); 4.4 (2H, s, NOCH$_2$CO); 6.4 (1H, s, 4-H); 6.8, 7.6 (1H each, s each, CH-imidazole).

Stage B —Cortisol-3-CMO (Syn)-[$^{125}$I] Iodohistamine Tracer

Labelling with iodine-125 carried out in a liquid medium involves the use of chloramine T as oxidising agent and sodium metabisulphite to stop the oxidation reaction. The iodination protocol is as follows: The labelling precursor obtained in stage A above, approx. 2 nanomoles, diluted in 60 $\mu$l of 0.2 M sodium phosphate buffer, pH 8.0, is treated with 20 $\mu$l of the solution of radioactive sodium iodide (1 nmol Na $^{125}$I) in the presence of 20 $\mu$l of 5 mg/ml of chloramine T solution in 0.2 M sodium-phosphate buffer, pH 8.0.

The mixture is allowed to incubate for 2 minutes at ambient temperature then the reaction is stopped by the addition of 100 $\mu$l of 1 mg/ml of aqueous solution of sodium metabisulphite. The reaction mixture is diluted in 700 $\mu$l of water, then separated by chromatography using a C18 $\mu$Bondapak column (reverse phase) according to the following elution conditions:

| Time (min) | Flow rate (ml/min) | Pump A (water) | Pump B (acetonitrile) |
| --- | --- | --- | --- |
| Initial | 1 | 90% | 10% |
| 5 | 1 | 90% | 10% |
| 80 | 1 | 50% | 50% |

Under these elution conditions the cortisol-3-CMO (syn)-[$^{125}$I] iodohistamine tracer is eluted at 49 min (37% acetonitrile).

EXAMPLE 5

Labelling Precursor: Isomer (Anti) of Cortisol-3-CMO Coupled to Histamine and the Corresponding Radioactive Iodinated Tracer

Stage A: Isomer (Anti) of Cortisol-3-CMO Coupled to Histamine

The isomer (anti) of cortisol-3-CMO activated in the form of N-hydroxysuccinimide ester obtained in stage A of example 3 is treated as described above in the case of the syn isomer to obtain the expected compound: cortisol-3-CMO (anti)-histamine.

$t_r$ (anti)=23.6 minutes (HPLC conditions mentioned above)

$R_f$=0.25 (chloroform-methanol-ammonia 60:10:2)

m.p.=134–138° C. (crude product separated by HPLC)

UV: $\lambda_{max}$=247 nm; $\epsilon$=23000 $M^{-1}cm^{-1}$ $^1$H-NMR (CD$_3$OD) δ0.87 (3H, s, 18-CH$_3$); 1.35 (3H, s, 19-CH$_3$); 2.8, 3.5 (2H each, t: J=7 Hz each, CH$_2$–CH$_2$-histamine); 4.2–4.7 (4H, q: J=19 Hz, 21-CH$_2$O); 4.4 (1H, m, 11α-H); 4.4 (2H, s, NOCH$_2$CO); 5.6 (1H, s, 4-H); 6.8, 7.6 (1H each, s each, CH-imidazole).

Stage B: Cortisol-3-CMO (Anti) -[$^{125}$I] Iodohistamine Tracer

Operations are carried out as indicated in stage B of example 4. The cortisol-3-CMO (anti)-[$^{125}$I] iodohistamine tracer is eluted at 46 minutes (35.6% acetonitrile).

EXAMPLE 6

Antibodies Induced by the Immunogen Cortisol-3-CMO (Syn)-BSA

Stage A —Immunization of Mice

Six-week old male Balb/c mice are immunized according to the following programme:

Day 0: Intraperitoneal injection of 50 μg of cortisol-3-CMO (syn)-BSA in a 50/50 emulsion (100 μl NaCl)/100 μl complete Freund's adjuvant).

Day 21: Repeat intraperitoneal injection with 50 μg of cortisol-3-CMO (syn)-BSA in a 50/50 emulsion (100 μl NaCl/100 μl incomplete Freund's adjuvant).

Day 42: Repeat intraperitoneal injection with 50 μg of cortisol-3-CMO (syn)-BSA in a 50/50 emulsion (100 μl NaCl/100 μl incomplete Freund's adjuvant).

Day 63: Repeat intraperitoneal injection with 50 μg of cortisol-3-CMO (syn)-BSA in a 50/50 emulsion (100 μl NaCl/100 μl incomplete Freund's adjuvant).

Day 84: Repeat intraperitoneal injection with 50 μg of cortisol-3-CMO (syn)-BSA in a 50/50 emulsion (100 μl NaCl/100 μl incomplete Freund's adjuvant).

Day 244: Intravenous injection of 100 μg of cortisol-3-CMO (syn)-BSA in 100 μl of NaCl and one hour afterwards, repeat intraperitoneal injection with 300 μg of this immunogen in 300 μl of NaCl.

Day 247: Cell fusion.

Stage B —Cell fusion according to the Köhler and Milstein protocol a) On day 247 the selected mouse is sacrificed and a sample of its spleen broken into pieces. The spleen cells are washed in the RPMI 1640 medium. The myeloma cells P3.X63.Ag8 653 cultivated beforehand in RPMI 20% foetal calf serum (FCS), 1% glutamine, 1% non-essential amino acids and 1% sodium pyruvate are also washed in the same medium.

In parallel, peritoneal macrophages are obtained by washing the peritoneum of non-immunized Balb/c mice with RPMI.

In order to obtain the formation of hybridomas, the spleen cells and the myeloma cells are mixed in a tube in a ratio of 5 spleen cells per myeloma cell. After centrifugation, the cell residue is resuspended in 800 μl of 50% polyethylene glycol 1500 in a 75 mM Hepes buffer, pH 7.5. After a contact time of 1 minute at 37° C., 20 ml of RPMI 1640 medium are added slowly to the fused cells.

b) The initial culture is produced in 96-well tissue culture plates in the presence of RPMI medium containing 20% foetal calf serum (FCS) and the following additives: hypoxanthine 5×10$^{-3}$M, aminopterin 2×10$^{-5}$M and thymidine 8×10$^{-4}$M. 5×10$^3$ peritoneal macrophages followed by 10$^5$ fused cells are added to each well.

Stage C —Cloning and Subcloning

Each hybridoma selected according to the method mentioned in stage D below results from a cloning by a maximum dilution technique in which 10, 5, 2, 1 and 0.5 cells are distributed randomly in microwells containing peritoneal macrophages. Two subcloning operations are thus carried out, each clone and sub-clone having been replicated then frozen in 90% FCS and 10% dimethylsulphoxide (DMSO). The sub-clones of the last generation finally undergo in vivo expansion to obtain ascitic fluid in Balb/c mice, followed by purification of the immunoglobulins on protein A.

Stage D —Technique for Selecting Hybrid Cells

Selection is carried out by a liquid phase radioimmunoassay technique starting with the culture supernatant. The supernatants possibly containing anti-cortisol antibodies are incubated with a solution of radioactive cortisol (tritiated cortisol or cortisol derivative labelled with radioactive iodine: cortisol-3-CMO (anti)-[$^{125}$I] iodohistamine). If anti-cortisol antibodies are present, they will bind the radioactive steroid. After incubation with charcoal-dextran and centrifugation to remove the free radioactivity and all the small molecules not fixed to the antibodies, a sample of the supernatant (bound fraction) is removed and counted.

Selection protocol

| Tubes | Culture supernatant | RPMI medium + 10% FCS | Mouse antiserum[1] | Tracer[2] | Buffer[3] |
| --- | --- | --- | --- | --- | --- |
| Tests | 70 μl | | | 100 μl | |
| Negative control | | 70 μl | | 100 μl | |
| Positive control | | | 70 μl | 100 μl | |
| Totals | | 70 μl | | 100 μl | 500 μl |

Incubation for 16 hours at 4° C.
Precipitation with 500 μl of charcoal[4]-dextran suspension for 15 minutes at
4° C. except in the "Totals" tubes
Centrifugation at 3,500 rpm for 15 minutes at 4° C.
Counting the radioactivity in a 550 μl sample of supernatant:
in the case of the tritiated tracer, counting is carried out on a beta counter after the addition of 6 ml of liquid scintillator
in the case of the iodinated tracer, counting is carried out directly on a gamma counter.

[1]Mouse antiserum induced by the immunogen cortisol-3-CMO (syn)-BSA in a 4,000-fold dilution in a 0.1M sodium phosphate buffer, 0.1% gelatin, 10 mM sodium azide pH 7.2
[2]Tracer: [1,2,6,7-$^3$H]cortisol (50–80 Ci/mmol), 10,000 cpm/100 μl 0.1M sodium phosphate buffer, 0.1% gelatin, 10 mM sodium azide, pH 7.2.
[2]Tracer: cortisol-3-CMO (anti)-[$^{125}$I] iodohistamine, 35,000 cpm/100 μl 0.1M sodium phosphate buffer, 0.1% gelatin, 10 mM sodium azide, pH 7.2.
[3]Buffer = 0.1M sodium phosphate, 0.1% gelatin, 10 mM sodium azide, pH 7.2.
[4]Suspension of charcoal-dextran cont. 0.3 g–0.03 g/100 ml of 0.1M sodium phosphate buffer, 0.1% gelatin, 10 mM sodium azide, pH 7.2.

The only cells retained during each cloning operation are those secreting the anti-cortisol antibodies that recognize both the tritiated cortisol tracer and the cortisol-3-CMO (anti)-[$^{125}$I] iodohistamine tracer, with a detection threshold greater than 5 times the negative sample.

The affinities of the monoclonal antibodies are measured by displacement of the cortisol-3-CMO (anti)-[$^{125}$I] iodohistamine tracer with the two labelling precursors: cortisol-3-CMO (anti)-histamine and cortisol-3-CMO (syn)-histamine. The affinity is estimated (in the form of the IC$_{50}$ value) according to the concentration displacing half of the tracer, since the tracer is present in a small quantity compared with the other constituents.

The table below shows the IC$_{50}$ values of two monoclonal antibodies obtained against the immunogen cortisol-3-CMO (syn)-BSA, in respect of which greater displacement of the cortisol-3-CMO (anti)-[$^{125}$I] iodohistamine by the syn isomer than by the anti isomer is observed.

| Monoclonal antibody | Displacement of the tracer by | | Ratio IC$_{50}$ anti/IC$_{50}$ syn |
|---|---|---|---|
| | Cortisol-3-CMO (anti)-histamine IC$_{50}$ (ng/ml) | Cortisol-3-CMO (syn)-histamine IC$_{50}$ (ng/ml) | |
| Immu 473 | 0.496 | 0.182 | 2.73 |
| Immu 482 | 0.468 | 0.176 | 2.66 |

The antibody IMMU-473 was selected in this way; it was filed and deposited with the Collection Nationale des Cultures de Microorganismes (CNCM) in Paris on Feb. 9, 1995 under number I-1532.

EXAMPLE 7

Kit for the Direct Determination of Cortisol in Sera or Plasma

The process mentioned is a competitive radioimmunoassay based on the following principle: the sera or plasma to be determined or the standards are incubated in tubes coated with anti-cortisol monoclonal antibodies according to the invention, with one or the other of the two cortisol-3-CMO (syn)-[$^{125}$I] iodohistamine or cortisol-3-CMO (anti)-[$^{125}$I] iodohistamine tracers. After incubation at 22° C., the contents of the tubes are removed by suction. The bound radioactivity is measured on a gamma counter. A calibration curve is prepared. The unknown values of the sera or plasma are determined by interpolation with the aid of this curve.

The reagents and protocol used for the direct determination of cortisol in sera and plasma are:

Reagents

Cortisol standard range in human serum from which steroids have been removed, and 20 mM sodium azide, pH 7.2, established for 6 concentrations: 0; 20; 70; 200; 700 and 2000 nM (0; 7.25; 25.37; 72.5; 253.75 and 725 ng/ml).

Cortisol-3-CMO (syn)-[$^{125}$I] iodohistamine or cortisol-3-CMO (anti)-[$^{125}$I] iodohistamine tracer of examples 4 and 5 adjusted to 150 000 cpm/ml of 0.1 M sodium phosphate buffer, 0.1% gelatin, 10 mM sodium azide and 3.56 μM danazol, pH 7.2.

Tubes coated with anti-cortisol monoclonal antibodies IMMU-473 according to the invention. The technique of coating these antibodies onto a solid phase is the one described in FR-A-2.543.972.

Test on 87 sera derived from patients

Protocol

25 μl of cortisol standard in human serum from which the steroids have been removed, or 25 μl of biological sample to be determined, and 0.5 ml of radiolabelled cortisol tracer are introduced into tubes coated with monoclonal antibodies according to the invention. After one hour's incubation at 22° C. with agitation (400 rpm), the contents of the tubes are removed and the bound radioactivity, immobilized in the tube, is measured on a gamma counter.

These direct determinations of cortisol according to the invention were compared with the determinations carried out after chromatography of the same sera on SEP PAK cartridges (Waters). FIG. 1 shows the correlation between the two methods of determination mentioned above. The values obtained by determination after chromatography are shown on the abscissa, and the values obtained by direct determination are shown on the ordinate, both being expressed in ng/ml. The results show a perfect correlation between these direct determinations and those carried out after chromatography (number of sera tested=87).

The Correlation is as Follows $Y_{(direct)} = 0.98 \ X_{(chromatography)} + 11.39$ $r = 0.92$ where Y represents the value obtained by direct determination, X represents the value obtained by determination after chromatography; r is the correlation coefficient.

EXAMPLE 8

Kits for the Direct Determination of Cortisol in Urine

This is also a competitive radioimmunoassay technique, the principle of which has already been described in example 7. In this process, the tubes coated with monoclonal antibodies IMMU-473 and the tracer, either cortisol-3-CMO (syn)-[$^{125}$I] iodohistamine or cortisol-3-CMO (anti)-[$^{125}$I] iodohistamine were the same as those used in the protocol for the direct determination of sera. Only the standard range is different: it is buffered, with a small quantity of bovine serum albumin (see below).

The reagents and the protocol applied in the direct determination of urine are as follows:

Reagents

Cortisol standard range in a 0.1 M sodium phosphate buffer, BSA 3 g/l, 20 mM sodium azide, pH 7.2, established for 6 concentrations: 0; 20; 70; 200; 700 and 2000 nM (0; 7.25; 25.37; 72.5; 253.75 and 725 ng/ml).

Cortisol-3-CMO (syn)-[$^{125}$I] iodohistamine or cortisol-3-CMO (anti)-[$^{125}$I] iodohistamine tracer adjusted to 150 000 cpm/ml of 0.1 M sodium phosphate buffer, 0.1% gelatin, 3.56 μM danazol, 10 mM sodium azide, pH 7.2.

Tubes coated with anti-cortisol monoclonal antibodies IMMU-473 according to the invention.

Test on 165 urine samples from patients

Protocol

50 μl of buffered cortisol standard or 50 μl of urine to be assayed are incubated in tubes coated with monoclonal antibodies IMMU-473 with 0.5 ml of cortisol-3-CMO (syn)-[$^{125}$I] iodohistamine or coritisol-3-CMO (anti)-[$^{125}$I] iodohistamine tracer. After one hour's incubation at 22° C. with agitation (400 rpm), the contents of the tubes are removed and the bound radioactivity, immobilized in the tube, is determined on the gamma counter.

We compared these direct determinations with those carried out after chromatography of the urine on SEP PAK cartridges (Waters).

Figure 2:
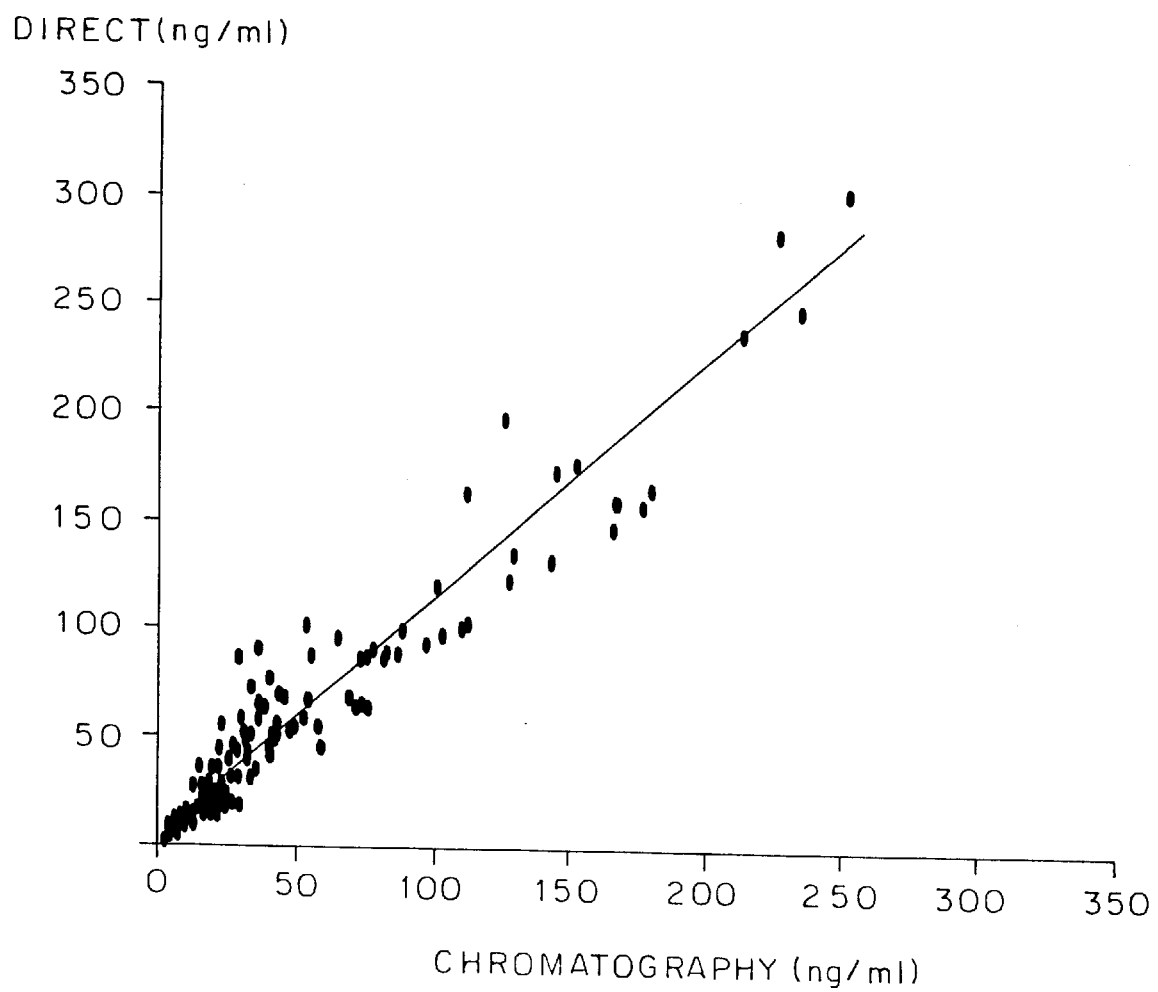
FIG. 2 shows the correlation between a direct determination of cortisol in urine and a method of determination of cortisol after chromatography of the urine.

FIG. 2 represents the correlation between the two methods of determination mentioned above for the 165 urine samples. The values obtained by determination after chromatography are shown on the abscissa and the values obtained by direct determination are shown on the ordinate, both sets of values being expressed in ng/ml. The correlation is very good:

$Y_{(direct)} = 1.09 \ X_{(chromatography)} + 5.3$ $r = 0.95$ where Y represents the value obtained by direct determination, X represents the value obtained by determination after chromatography; r is the correlation coefficient.

Table 2 below shows the results obtained using two processes for the direct determination of cortisol in the urine of the prior art compared with the process according to the invention, and to the reference process after chromatography. Only the process according to the invention gives exact results; the two other processes overestimate the concentrations of the urine samples by a factor of 2, on average.

TABLE 1

Various cortisol assay kits on the market

| Manuf. | Kodak | Orion | DSL | Incstar | Radim | Diagnostic Pasteur | DPC | Corning | ICN | Immunotech 1st generation | Biomerica | Eurogenetics |
|---|---|---|---|---|---|---|---|---|---|---|---|---|
| Ref. | IM-2021 | 68548 | DSL 2000 | CA-529 | KS 18 CT | 825 | TK COI | 472.360 Magic | 07.22 1102 | 1114 | 1019 | Cortisol Elisa |
| Assay technique | RIA | RIA | RIA | RIA | RIA | RIA | RIA | RIA | RIA | RIA | EIA | EIA |
| Serum | direct | direct | direct | direct | direct | direct | direct | direct | direct | direct | direct | direct |
| Urine | direct | direct or extrac. | direct or extrac. | extraction | extraction | extraction | extraction | extraction | extraction | direct extraction | direct extraction | extraction |

TABLE 2

CORTISOL CONCENTRATION (ng/ml)

| KITS URINE | Orion direct | Kodak direct | Present invention | Chromatography |
|---|---|---|---|---|
| A | 27 | 19 | 10 | 8 |
| B | 9 | 10 | 8 | 8 |
| C | 23 | 24 | 15 | 11 |
| D | 48 | 35 | 18 | 19 |
| E | 38 | 42 | 20 | 21 |
| F | 62 | 66 | 36 | 33 |
| G | 63 | 55 | 34 | 33 |
| H | 85 | 73 | 40 | 45 |
| I | 110 | 84 | 45 | 48 |
| J | 101 | 84 | 47 | 59 |
| K | 175 | 105 | 56 | 64 |
| L | 417 | 253 | 158 | 166 |

These results show the good correlation obtained between the process of the present invention and the reference method (chromatography) for each urine sample tested.

What is claimed is:

1. A monoclonal antibody which specifically binds cortisol in urine without interference by urine constituents, wherein:
said monoclonal antibody binds $^{125}$I-labeled derivatives of cortisol-3-carboxymethyloxime(anti)-histamine and $^{125}$I-labeled derivatives of cortisol-3-carboxymethyloxime(syn)-histamine with the same affinity; and
said monoclonal antibody binds unlabeled derivatives of cortisol-3-carboxymethyloxime (anti)-histamine isomer and cortisol-3-carboxymethyloxime(syn)-histamine isomers with a ratio of affinities (IC$_{50}$) greater than 1 in favor of the syn isomer.

2. The monoclonal antibody in accordance with claim 1 produced by hybridoma IMMU-473 having Collection Nationale des Cultures de Microorganismes accession number I-1532.

3. A kit for the direct assay of cortisol in urine without prior treatment of a urine sample, comprising:
a monoclonal antibody according to claim 1;
a tracer selected from the group consisting of $^{125}$I-labeled derivatives of cortisol-3-carboxymethyloxime(anti)-histamine, $^{125}$I-labeled derivatives of cortisol-3-carboxymethyloxime(syn)-histamine, and a mixture thereof; and
a set of cortisol standards.

4. A method for the assay of cortisol in urine without prior treatment of a urine sample, comprising the steps of:
contacting a urine sample with a monoclonal antibody according to claim 1 wherein the antibody is immobilized on a solid support, and with a tracer selected from the group consisting of $^{125}$I-labeled derivatives of cortisol-3-carboxymethyloxime(anti)-histamine, $^{125}$I-labeled derivatives of cortisol-3-carboxymethyloxime (syn)-histamine, and a mixture thereof;
separating unbound tracer from bound tracer;
detecting the bound tracer; and
determining the amount of cortisol present in the urine sample by interpolation of said detected bound tracer to a standard curve.

5. A monoclonal antibody which specifically binds cortisol in urine without interference by urine constituents, wherein:
said monoclonal antibody binds $^{125}$I-labeled derivatives of cortisol-3-carboxymethyloxime(anti)-histamine and $^{125}$I-labeled derivatives of cortisol-3-carboxymethyloxime(syn)-histamine with the same affinity; and
said monoclonal antibody binds unlabeled derivatives of cortisol-3-carboxymethyloxime(anti)-histamine isomer and cortisol-3-carboxymethyloxime(syn)-histamine isomers with a ratio of affinities (IC$_{50}$) greater than 1.5 in favor of the syn isomer.

6. The monoclonal antibody in accordance with claim 5 produced by hybridoma IMMU-473 having Collection Nationale des Cultures de Microorganismes accession number I-1532.

7. A kit for the direct assay of cortisol in urine without prior treatment of a urine sample, comprising:
a monoclonal antibody according to claim 5;
a tracer selected from the group consisting of $^{125}$I-labeled derivatives of cortisol-3-carboxymethyloxime(anti)-histamine, $^{125}$I-labeled derivatives of cortisol-3-carboxymethyloxime(syn)-histamine, and a mixture thereof; and
a set of cortisol standards.

8. A method for the assay of cortisol in urine without prior treatment of a urine sample, comprising the steps of:
contacting a urine sample with a monoclonal antibody according to claim 5 wherein the antibody is immobilized on a solid support, and with a tracer selected from the group consisting of $^{125}$I-labeled derivatives of cortisol-3-carboxymethyloxime(anti)-histamine, $^{125}$I-labeled derivatives of cortisol-3-carboxymethyloxime (syn)-histamine, and a mixture thereof;

separating unbound tracer from bound tracer;

detecting the bound tracer; and determining the amount of cortisol present in the urine sample by interpolation of said detected bound tracer to a standard curve.

\* \* \* \* \*